(12) United States Patent
Greenfield et al.

(10) Patent No.: US 6,689,904 B2
(45) Date of Patent: Feb. 10, 2004

(54) BRIDGED TRICYCLIC ANALOGS OF 2-(CARBOXYCYCLOPROPYL)GLYCINE

(75) Inventors: Alexander Alexei Greenfield, Princeton Junction, NJ (US); John Anthony Butera, Clarksburg, NJ (US)

(73) Assignee: Wyeth, Madison, NJ (US)

( * ) Notice: Subject to any disclaimer, the term of this patent is extended or adjusted under 35 U.S.C. 154(b) by 34 days.

(21) Appl. No.: 10/185,445

(22) Filed: Jun. 27, 2002

(65) Prior Publication Data

US 2003/0018065 A1 Jan. 23, 2003

Related U.S. Application Data

(60) Provisional application No. 60/302,251, filed on Jun. 29, 2001.

(51) Int. Cl.[7] ............................................... C07C 61/12
(52) U.S. Cl. ........................................................ 562/499
(58) Field of Search ........................................ 562/499

(56) References Cited

U.S. PATENT DOCUMENTS 6,124,361 A    9/2000   Chenard

FOREIGN PATENT DOCUMENTS

| EP | 0 363 994 A2 A3 | 4/1990 |
| EP | 0 363 994 B1 | 9/1993 |
| WO | WO 99/47490 A1 | 9/1999 |

OTHER PUBLICATIONS

U.S. patent application Ser. No. 10/185,466, Baudy et al., Not Published.
U.S. patent application Ser. No. 10/185,489, Stack et al., Not Published.
L. Fowden et al., Phytochemistry, 8, 437–443, (1969).
S. Hirsch et al., Pharmacology Biochemistry & Behavior, 56(4), 797–802, (1997).
Y. Hayashi et al., Br. J. Pharmacol., 107, 539–543 (1992).
E. Ndzie, et al., Tetrahedron: Asymmetry, 8(17), 2913–2920, (1997).
J. Monn et al., J. Med. Chem., 42, 1027–1040, (1999).
F. Tellier et al., Bioorganic & Medicinal Chemistry, 6, 195–208, (1998).
F. Trigalo et al., Tetrahedron, 46(15), 5203–5212, (1990).
F. Tellier et al., Bioorganic & Medicinal Chemistry Letters, 5(22), 2627–2632, (1995).
K. Alder et al., Chem. Ber., GE, 93, 2271–2281, (1960).
W. Danysz et al., Behavioral Pharmacology, 6, 455–474, (1995).
A. Carlsson et al., Int. Acad. Biomed. Drug Resch., 4, 118–129, (1993).
E. Frittoli et al., Neuropharmacology, 33(6), 833–835, (1994).
P. Freeman et al., The Journal of Organic Chemistry, 33(6), 2211–2214, (1968).
J.A. Monn et al., J. Med. Chem., 40, 528–537 (1997).
A.P. Kozikowski et al., J. Med. Chem., 41, 1641–1650 (1998).

*Primary Examiner*—Paul J. Killos
(74) *Attorney, Agent, or Firm*—Kimberly R. Hild

(57) ABSTRACT

This invention provides processes for preparing a group of novel bridged tricyclic compounds having the formula:

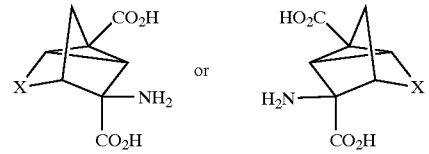

wherein X is $(CH_2)_n$, O, S, SO, $SO_2$ or $CR^1R^2$; n is 1 or 2; and $R^1$ and $R^2$ are, independently, hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl.

9 Claims, No Drawings

BRIDGED TRICYCLIC ANALOGS OF 2-(CARBOXYCYCLOPROPYL)GLYCINE

This application claims priority from co-pending provisional application serial No. 60/302,251, filed on Jun. 29, 2001, the entire disclosure of which is hereby incorporated by reference.

This invention relates to novel bridged trycyclic analogs of 2-(carboxycyclopropyl)glycine which are selective inhibitors of human type 2 excitatory amino acid transporters (EMT-2). More particularly, this invention provides a process for preparing these compounds.

BACKGROUND OF THE INVENTION

Conformationally restricted glutamate analogs, that are selective inhibitors of human type 2 excitatory amino acid transporters (EAAT2) may thus serve to increase synaptic glutamate levels by inhibiting glutamate re-uptake and are useful for treatment of diseases characterized by glutamate hypofunction, such as schizophrenia, schizoaffective disorder and schizophreniform disorder (Int. Acad. Biomed. Drug Res. Basel, Karger, 1993, vol. 4, p. 118–129; Pharmacol., Biochem. Behav. (1997), 56(4), 797–802), with particular effectiveness against the negative symptoms of schizophrenia, and for the treatment of conditions which, though not necessarily caused by glutamate hypofunction, are nonetheless responsive to treatment by increased glutamate, such as the cognitive deficits due to aging, stroke, Alzheimer's disease or other neurodegenerative diseases, or schizophrenia (Behav. Pharmacol. (1995), Date 1995, Volume 6(5 & 6), 455–74). The compounds of this class are also useful as selective tools for the investigation of excitatory amino acid transport, especially for the identification of agents which selectively stimulate glutamate re-uptake and thus provide a neuroprotective effect for patients who have suffered stroke or head trauma.

WO 9947490, for example, claims a series of compounds described by the formula below in which n is 0–6, X is $CH_2$, $CH_2CH$ or O, Z is $CHR^2$ or $NR^2$ and $R^1$ and $R^2$ are hydrogen, alkyl, aryl or heteroaryl as metabotropic glutamate receptor ligands useful for the treatment of a variety of neurological and psychiatric disorders.

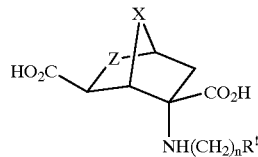

The 2-(carboxycyclopropyl)glycines (CCG's) are conformationally restricted glutamate analogs and consist of eight isomers including L- and D-enantiomers. L-CCG-I, [(2S, 3S,4S-CCG] isolated by Fowden et al. (Phytochemistry 1969, 8, 437) from immature fruits of *Aesculus parviflora* and *Blighia sapida* has been shown (Br. J. Pharmacol. 1992, 107, 539) to be a potent agonist for type 2 metabotropic glutamate receptors (mGluR2). L-CCG-III [(2S,3S,4R)-CCG], on the other hand, is a potent and competitive inhibitor of both glial and neuronal uptake of glutamate (Neuropharmacology 32, 833). EP0363994 claims the preparation of (2R,3S,4S)-alpha-(carboxycyclopropyl) glycine

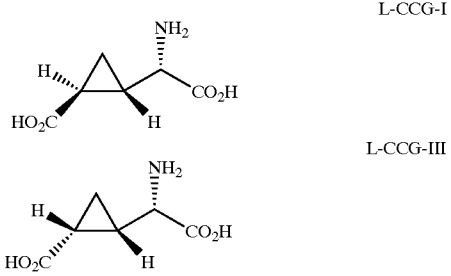

as an N-methyl-D-aspartic acid (NMDA) agonist useful as a tool to investigate various neuronal functions related to the excitatory amino acid receptors.

WO 9947490 claims a series of compounds described by the formula below in which n is 0–6, X is $CH_2$, $CH_2CH$ or O, Z is $CHR^2$ or NR and $R^1$ and $R^2$ are hydrogen, alkyl, aryl or heteroaryl as metabotropic glutamate receptor ligands useful for the treatment of a variety of neurological and psychiatric disorders.

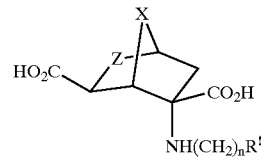

U.S. Pat. No. 6,124,361 (Chenard) teaches substituted bicyclo[3.1.0]hexane compounds of the formula:

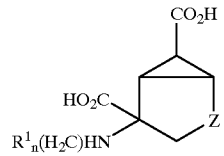

wherein n is an integer from 0 to 6; Z is ($C_1$–$C_4$) alkylene, oxygen, sulfur, NH or N($C_1$–$C_6$)alkyl; and $R^1$ is H or optionally substituted aryl or heteroaryl; which are metabotropic glutamate receptor ligands useful in the treatment of a variety of neurological and psychiatric disorders.

The process described in the invention can be used for preparation of the novel restricted glutamate analogs. Known syntheses (prior art) of restricted glutamate analogs usually entail preparation of diastereomers, followed by their separation, removal of chiral auxiliary and, sometimes anion-exchange chromatography. The later processes are known to be time consuming, expensive and labor intensive. The present invention represents an alternative, more efficient process. It replaces precious chiral auxiliary with inexpensive non-chiral reagents. The reagents provide reliable protection in one simple step. Moreover, the process simultaneously introduces a chromophore, nitrogen protection and lipophilic load to simplify monitoring, hydrolysis and isolation/separation procedures. The process also allows for amplification of stereochemical bias of the corresponding derivatives that facilitates their chiral separation.

Disclosed herein process utilizes chiral chromatography, where chiral phase can be reused, rather than chiral auxiliary, where the latter is subsequently discarded or, sometimes, impractical to recover.

DESCRIPTION OF THE INVENTION

This invention provides a process for preparing a group of novel bridged tricyclic compounds having the formula:

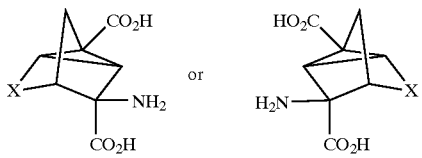

wherein
X is $(CH_2)_n$, O, S, SO, $SO_2$ or $CR^1R^2$;
n is 1 or 2;
$R^1$ and $R^2$ are, independently, hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;
the process comprising the steps of:
a) treating keto-acid of formula (1):

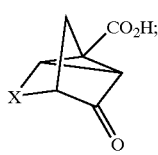

(1)

in the presence of ammonium carbonate and an alkali metal cyanide, such as potassium cyanide, in a volume of organic solvent/water to give a spiro-fused hydantoin as a mixture of diastereomers having the formula (2);

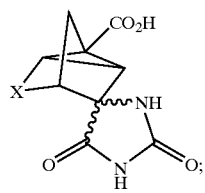

(2)

b) treating the spiro-fused hydantoin mixture of diastereomers (2) with an appropriate benzylic halogenide or sulfonate and alkali metal carbonate in an aprotic solvent to provide tri-substituted diastereomeric mixture of hydantoins (3);

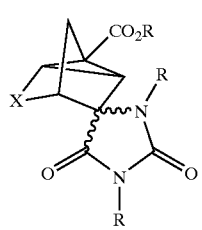

(3)

wherein R represents the benzyl residue of the corresponding benzylic halogenide or sulfonate;
c) Separating the exo- and endo-racemic pairs of tri-substituted diastereomeric mixture of hydantoins (3) to yield the racemic mixture of (4) and (4');

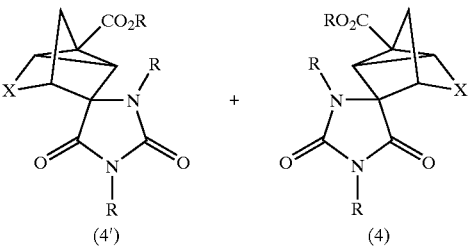

d) Resolving the racemic mixture of (4) and (4') on a chiral column to produce both enantiomers (4) and (4') in an enantiomerically pure form;
e) treating intermediates (4), (4'), or a mixture thereof, with base to provide enantiomers of the formulae (5) and (5'):

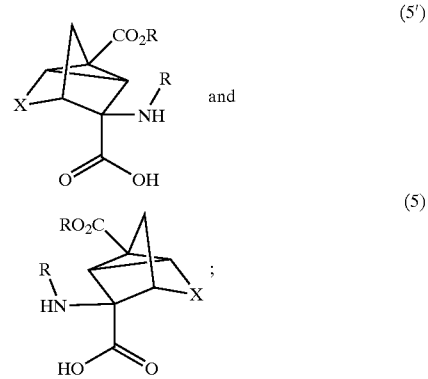

f) treating the compounds (5) and (5') with a palladium on carbon catalyst to provide the dextro-(+) and levorotatory (−) forms of the compounds (6') and (6).

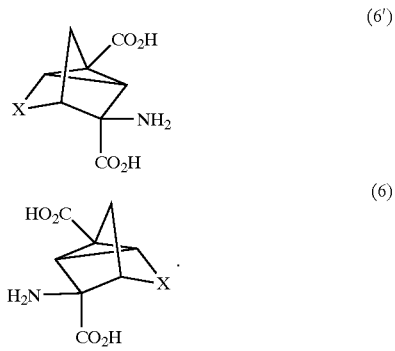

An additional and optional step of this process comprises the formation of a pharmaceutically acceptable salt form of a compound of formulae (6) or (6'). This salt formation may be completed by methods known in the art.

The process of this invention may be conducted in a solvent mixture of an organic solvent and water, preferably at an organic solvent/water ratio of from about 1:1 to about 4:1, more preferably at a ratio of from about 2.5/1 to about 1.5/1, most preferably about 2:1. Acceptable organic solvents are those known in the art to be miscible in water including, but not limited to, acetonitrile, acetone, tetrahydrofuran (THF), dimethylformamide (DMF), N-methylpyridine, N-methylpyrrolidone, dimethylsulfoxide (DMSO), sulfalane, $C_1$–$C_8$ alkanols (including methanol and ethanol), glymes, such as monoglyme (1,2-Dimethoxyethane), or $C_2$–$C_8$ glycols.

Treating of the keto acid of formula (1) in step a), above, may be conducted at room temperature or with heating. Preferably, heating of the solvent mixture during this step may be from room temperature up to the boiling point of the water in the solvent mixture, though higher temperatures may be utilized under pressure.

In step b) of the process, the benzylic halogenide or sulfonate may be any synthetically useful substituted or unsubstituted benzylic halogenide or sulfonate. Among the most preferred of these groups are benzyl halogenide or benzyl sulfonate groups, either unsubstituted or substituted by from 1 to 3 groups the same or different selected from halogen, $C_1$–$C_6$ alkyl, $C_1$–$C_6$ alkoxy, $C_1$–$C_6$ thioalkyl, —$CF_3$, —CN, —OH, —$NH_2$, —$CH_2$—($C_3$–$C_6$ cycloalkyl), etc. The halogen portion of the benzylic halogenides is preferably 1, Br or Cl. Among the more preferred sulfonates are the benzyl sulfonates including benzyl sulfonate, benzyl mesylate, benzyl tosylate, benzyl nosylate, benzyl triflate, etc. In addition, equivalent alkylating agents known in the art may be used in step b) of this process. It will be understood that the R residue in the process formulas listed above indicates the remaining residue from the relevant alkylating agent. For instance, a para-fluoro benzyl residue will be left as a substituent from reaction with para-fluoro benzyl bromide. Alkali metal carbonates useful in this process include sodium carbonate, lithium carbonate and potassium carbonate.

Aprotic solvents useful herein include those known in the art, including, but not limited to, DMF, DMSO, acetonitrile, etc.

In step d), it will be understood that the enantiomers (4) and (4') will be separated from each other to produce individual compositions in substantially or fully enantiomerically pure form. Enantiomerically pure form is understood herein to indicate the purity understood in the art for such forms, preferably indicating a concentration of one enantiomer being 99% or greater in the composition relative to the other. More preferably the composition comprises 99.5% or greater of the desired enantiomer, most preferably 99.9% or greater. In the most preferred situation, the undesired enantiomer will be undetectable in the composition by conventional industrial means.

Commercially available chiral columns, such as those available in the Whelk-O 1 line of spherical silica, irregular silica and spherical Kromasil silica columns available from Regis Technologies, Inc., Morton Grove, Ill., U.S.A., or the chiral columns available under the CHIRALCEL® and CHIRALPAK® marks from Merck Eurolab Ltd., may be used in step d). It will be understood that other commercially available and art recognized columns and column materials useful for chiral chromatography may be used with the process of this invention.

The hydrolysis of step e) is preferably carried out in the same solvent mixture(s) as described above for step a), preferably with heating. Preferably, the step may be conducted at a temperature of from about 60° C. to about 180° C., more preferably from about 80° C. to about 160° C. Among the preferred bases for step e) are the alkali bases known in the art, including barium hydroxide, calcium hydroxide, lithium hydroxide, sodium hydroxide, potassium hydroxide, etc. It will be understood that the concentration of base in this step will effect the time required for completion. Preferably, the concentration of base will be from about 0.25N to the saturation point of the base in the organic solvent of the solvent mixture. More preferably, the base concentration will be 0.5N or higher. A specific example of a useful base is sodium hydroxide at a concentration of from about 1.5 N to about 3.0 N.

A preferred group of compounds of this invention are those in which $R^1$, $R^2$ and n are defined as above, X is $(CH_2)_n$, O or $CR^1R^2$, $R^3$, $R^4$ and $R^5$ are hydrogen and Z is hydrogen or alkyl of one to six carbon atoms. Most preferred are those examples in which n is defined as above, X is $(CH_2)_n$, O or $CR^1R^2$, wherein $R^1$ and $R^2$ are, independently, hydrogen, halogen, hydroxy, alkyl of one to six carbon atoms or alkoxy of one to six carbon atoms and $R^3$, $R^4$, $R^5$ and Z are hydrogen.

One process of this invention includes preparation by the methods herein of compounds of the formulae:

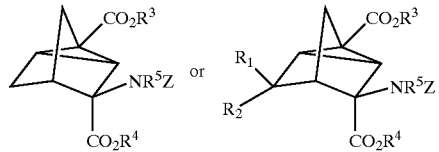

wherein:

$R^1$ and $R^2$ are independently selected from hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;

or a pharmaceutically acceptable salt thereof.

Of these compounds, the preferred members are those in which $R^1$, $R^2$ and n are defined as above, X is $(CH_2)_n$, O or $CR^1R^2$, $R^3$, $R^4$ and $R^5$ are hydrogen and Z is hydrogen or alkyl of one to six carbon atoms. Most preferred are those examples in which n is defined as above, X is $(CH_2)_n$, O or $CR^1R^2$, wherein $R^1$ and R are, independently, hydrogen, halogen, hydroxy, alkyl of one to six carbon atoms or alkoxy of one to six carbon atoms and $R^3$, $R^4$, $R^5$ and Z are hydrogen. This invention relates to the process of preparation of both enantiomers of the bridged tricyclic aminodicarboxylic acid described above, as well as to mixtures of the enantiomers. Throughout this application, the name of the product of this invention, where the absolute configuration or the optical rotation of the bridged tricyclic aminodicarboxylic acid is not indicated, is intended to embrace the individual enantiomers as well as mixtures of the two. When it is necessary to distinguish the enantiomers from one another and from the racemate, the sign of the optical rotation [(+), (−) and (+/−)] is utilized. Furthermore, throughout this application, the designations R* and S* are used to indicate relative stereochemistry, employing the Chemical Abstracts convention which automatically assigns R* to the lowered numbered asymmetric center. While the above genus is intended to embrace both diastereomers about the amino acid α-carbon, the R* configuration is preferred.

The compounds, whose process of preparation is described herein have potent and selective inhibitory effect on human EAAT2 and thus are useful in the treatment of disorders such as schizophrenia, schizoaffective disorder and schizophreniform disorder, which are characterized by glutamate hypofunction, and for the treatment of cognitive deficits due to aging, stroke, Alzheimer's disease or other neurodegenerative diseases, or schizophrenia. The compounds of the invention are especially useful as tools to investigate various neuronal and glial functions related to excitatory amino acid transport.

Alkyl as used herein refers to an aliphatic hydrocarbon chain and includes straight and branched chains such as methyl, ethyl, n-propyl, n-butyl, isobutyl, sec-butyl, t-butyl, n-pentyl, isopentyl, neopentyl, n-hexyl and isohexyl.

Halogen (or halo) as used herein refers to chlorine, bromine, fluorine and iodine.

Alkoxy as used herein refers to the group R—O— where R is an alkyl group of 1 to 6 carbon atoms.

Alkylidene as used herein refers to the group $R^6R^7C$=C where $R^6$ and $R^7$ are independently hydrogen or alkyl groups of 1 to 5 carbon atoms, the group having from 1 to 6 carbon atoms.

The pharmaceutically acceptable salts are those derived from such organic and inorganic acids as: acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids. Alternatively, the compounds of the invention which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di- and trimethyl-ammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropyl-pyrrolidinium, 1,4-dimethylpiperazinium, 1-n-butylpiperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The bridged tricyclic aminodicarboxylic acids of the invention are prepared as illustrated below. Specifically, the appropriately substituted cyclic diene is caused to undergo a Diels-Alder reaction with α-chloroacrylonitrile by refluxing in a suitable solvent such as benzene or toluene to give the bicyclic α-chloronitrile as a mixture of diastereomers. Hydrolysis of the α-chloronitrile with potassium hydroxide in a mixture of ethanol and water is accompanied by participation of the double bond and yields a bridged tricyclic hydroxy acid.

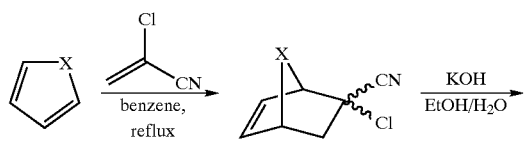

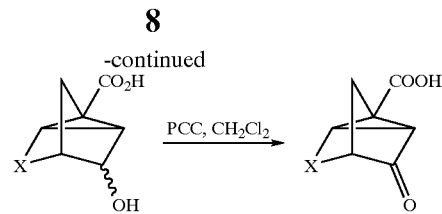

The hydroxy group of the latter converted to the carbonyl by treatment with a suitable oxidant such as pyridinium chlorochromate (PCC) or the Swern reagent. The synthesis of (1) where X=CH$_2$ has been described in Chem.Ber., GE, 93, 1960, 2271–2281.

The compounds described in the Formula can be prepared as illustrated below in Scheme 1. The process described herein can be used to make dextro-(+) and levorotatory (−) forms of the compounds of the Formula, as well as the racemic mixtures.

Keto acid (1) (Scheme 1) is subjected to the classical Bucherer-Bergs conditions (ammonium carbonate and alkali metal cyanide in ethanol/water) to give a spiro-fused hydantoin as a mixture of diastereomers (2). The latter is exhaustively benzylated using appropriate benzyl halogenide and alkali metal carbonate in DMF or other aprotic solvent to afford tri-benzylated diastereomeric mixture of hydantoins (3). Separation of exo- and endo-racemic pairs is accomplished using, for example, normal phase HPLC on Silica column to yield the racemic mixture of (4) and (4'), which is further resolved on chiral column, such as Whelk-O, to produce both enantiomers (4) and (4') in pure form (>99% enantiomeric excess) with no loss of material.

The individual enantiomers are separately deprotected by successive treatment with the base, such as 2.5 N sodium hydroxide at elevated temperature and hydrogenolysis over palladium on carbon to provide the dextro-(+) and levorotatory (−) forms of the title compound (6') and (6).

Scheme 1

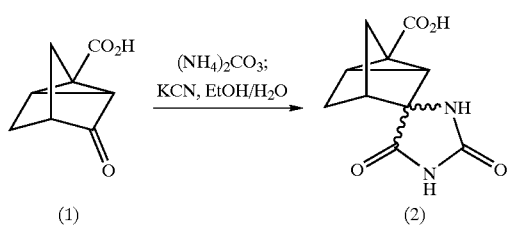

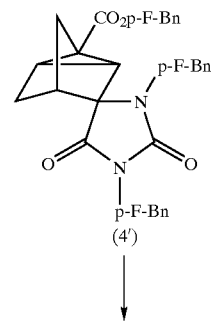

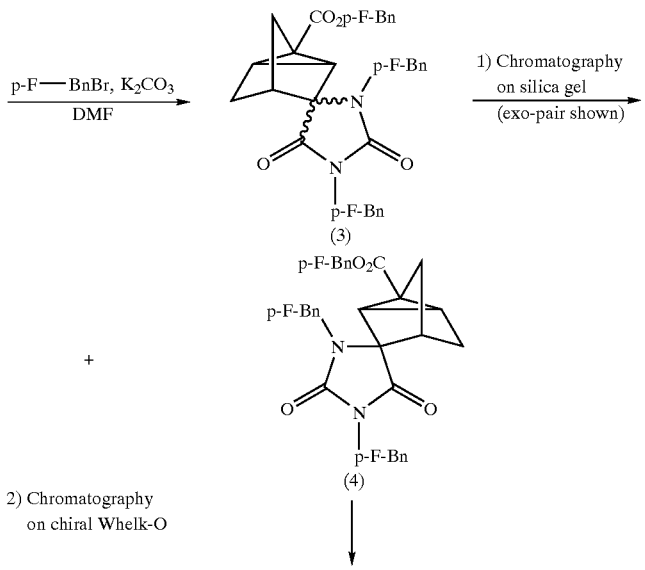

2) Chromatography on chiral Whelk-O

-continued
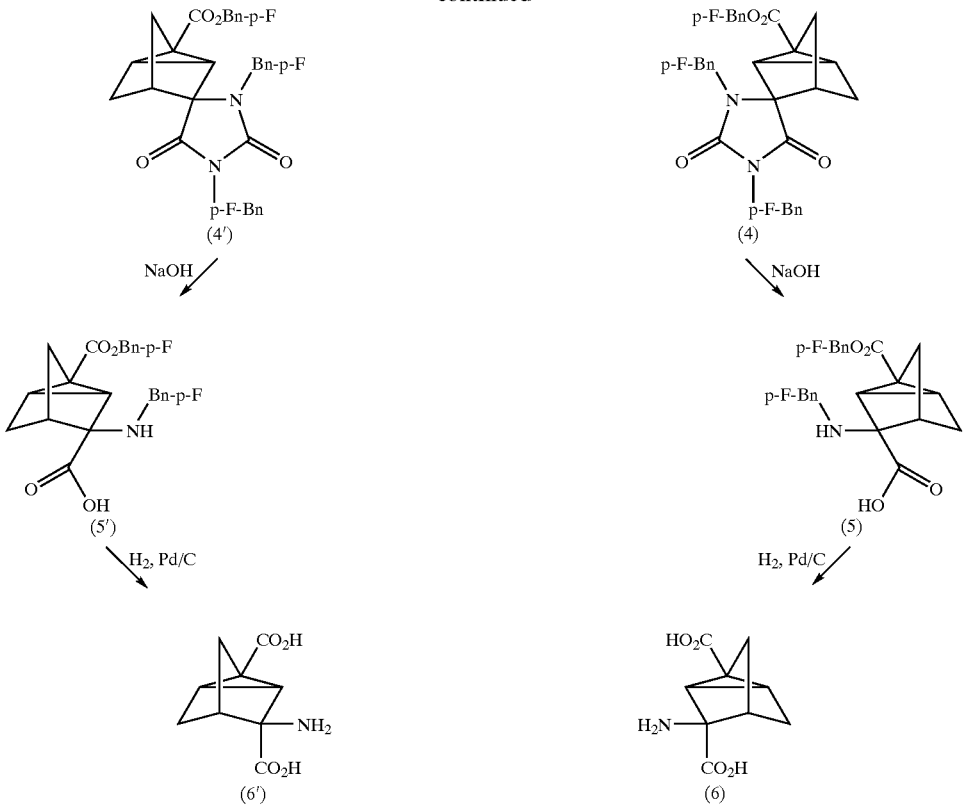
Alternatively, the compounds disclosed in the Formula can be prepared according to Scheme 2. The process described herein can be used to make dextro-(+) and levorotatory (−) forms of the compounds of the Formula, as well as the racemic mixtures.
Scheme 2
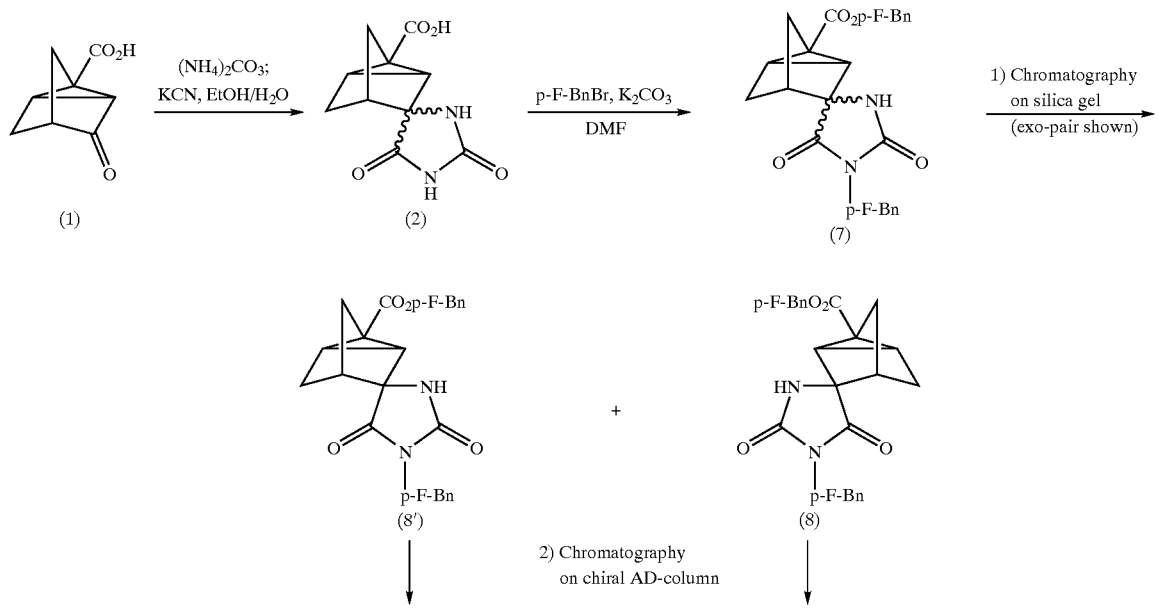

-continued

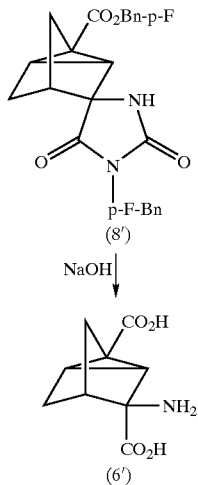

(8')

NaOH ↓

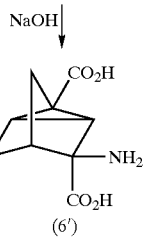

(6')

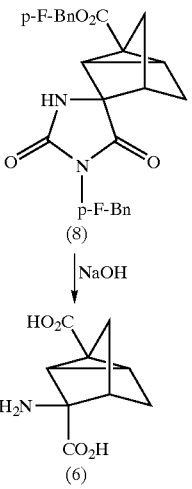

(8)

NaOH ↓

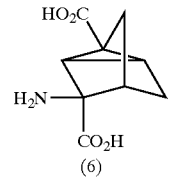

(6)

Keto acid (1) (see above) is subjected to the classical Bucherer-Bergs conditions (ammonium carbonate and alkali metal cyanide, such as potassium cyanide, in ethanol/water) to give a spiro-fused hydantoin as a mixture of diastereomers (2). The latter is partially benzylated using appropriate benzyl halogenide and alkali metal carbonate in DMF or other aprotic solvent to afford di-benzylated diastereomeric mixture of hydantoins (7). Separation of exo- and endo-racemic pairs is accomplished using, for example, normal phase HPLC on Silica column to yield the racemic mixture of (8) and (8'), which is further resolved on chiral column, such as AD-Chiralcel, to produce both enantiomers (8) and (8') in pure form (>99% enantiomeric excess) with no loss of material. The ammonium carbonate and alkali metal cyanide compounds of this step may be used at concentrations known in the art, such as a concentration from about 0.1M to the saturation point of the compound in the reaction medium. A more preferable concentration would be from about 0.5M to about 3M.

The individual enantiomers are separately deprotected by treatment with the base, such as 2.5 N sodium hydroxide at elevated temperature to provide the dextro-(+) and levorotatory (−) forms of the title compounds (6') and (6).

The racemic mixture of (6) and (6') can be produced by deprotection with sodium hydroxide of a racemic mixture of (8) and (8').

The following examples illustrate the production of representative compounds of this invention.

EXAMPLE 1

(−)-(1R*,2R*,3R*,4S*,6S*)-3-aminotricyclo[2.2.1.0$^{2,6}$] heptane-1,3-dicarboxylic Acid The synthesis of (−)-(1R*,2R*,3R*,4S*,6S*)-3-aminotricyclo[2.2.1.0$^{2,6}$]heptane-1,3-dicarboxylic acid has been accomplished in accordance with Scheme 1. The starting material, racemic 3-oxo-tricyclo[2.2.1.0$^{2,6}$]heptane-1-carboxylic acid (1), was prepared according Chem.Ber., GE, 93, 1960, 2271–2281. The crude material of ~80% purity was used without further purification.

Intermediate (2)-2',5'-Dioxo-spiro{tricyclo[2.2.1.0$^{2,6}$] heptane-3,4'-imidazoline}-1-carboxylic Acid.

A mixture of 1.52 g (10 mmol) of ketoacid (1), 0.78 g (12 mmol) of KCN and 3.36 g (35 mmol) of $(NH_4)_2CO_3$ in 75 mL of water-ethanol (1:1) was stirred at 75° C. for 36 hrs (additional 2–4 mmol of KCN and 6–12 mmol of ammonium carbonate added after 18 hrs). After completion most of ethanol was evaporated, reaction mixture acidified to pH=1 with concentrated HCl. Upon cooling the mixture to 0° C., a white precipitate formed and was washed with ice-cold water and ethyl acetate and dried in vacuum affording ~1.32 g (6 mmol) of hydantoin. Additional 0.22 g (~1 mmol) was isolated after concentration of mother liquor to the total yield of 1.54 g (7 mmol) (88% on pure ketoacid 1). The product was used as such without additional purification.

Intermediate (3)-1',3'-di-(4-fluorobenzyl)-2',5'-dioxo-spiro{tricyclo[2.2.1.0$^{2,6}$]-heptane-3,4'-imidazoline}-1-carboxylic Acid 4-fluorobenzyl Ester.

A solution of 1.1 g (5 mmol) of 2',5'-dioxo-spiro{tricyclo [2.2.1.0$^{2,6}$]heptane-3,4'-imidazoline}-1-carboxylic acid (2) in 30 mL of N, N-dimethylformamide was treated with an excess of p-fluorobenzyl bromide 4.73 g (25 mmol) and $K_2CO_3$ (3.45 g, 25 mmol) at 60° C. for 36 hrs. After cooling to room temperature, the mixture was diluted to 500 mL with water and extracted with 2×250 mL of ethyl acetate. The extracts were washed with water, dried over sodium sulfate and concentrated in vacuum to give 2.7 g of the title compound (3) as a mixture of diastereoisomers.

A mixture of diastereoisomers of 1',3'-di-(4-fluorobenzyl)-2',5'-dioxo-spiro{tri-cyclo[2.2.1.0$^{2,6}$] heptane-3,4'-imidazoline}-1-carboxylic acid 4-fluorobenzyl ester (6.7 g material (3) from several reactions) was chromatographed using HPLC (Primesphere 10 Silica column 50×250 mm, 95 mL/min 24% ethyl acetate/hexane) to give the individual diastereomers of the title compound, each as a racemic mixture (in a ratio ~1.5–2:1 in a favor of precursor (4+4')). The major product, the precursor of the (R*) amino acid was the first to elute (retention time 12.1 min) and 3.0 g was obtained as a colorless foam upon concentration in vacuum.

This was resolved into the individual enantiomers (4) and (4') with no loss of material on chiral Whelk-O column (2×25 cm, ethanol:hexane=1:1, flow rate 20 mL/min). Evaporation of solvent afforded 1.5 g of intermediate (4) from the first fraction and 1.5 g of intermediate (4') from the second fraction.

(−)-(1R*,2R*,3R*,4S*,6S*)-3-aminotricyclo[2.2.1.0$^{2,6}$] heptane-1,3-dicarboxylic Acid 1.1 g (2 mmol) of intermediate (4)—the first enantiomer to elute from the chiral HPLC chromatography described in the above procedure (retention time 6.6 min on analytical Whelk-O 1 (Regis Technologies, Inc., Morton Grove, Ill., U.S.A.) column, eluent—50:50 ethyl acetate/hexane, 1 mL/min) was subjected to a hydrolysis in a stirred mixture of 2.5 N NaOH (30 mL)—methanol (10 mL) in a stainless steel autoclave at 160° C. for 32 hrs. After completion of the reaction methanol was evaporated, the mixture was extracted with ethyl acetate. The water layer was acidified to pH=3–3.4 and evaporated to dryness. Dry solid was reconstituted with minimal amount of cold acidic (pH=3) water to dissolve inorganics and filtered to afford after washing with ethyl acetate and drying 0.62 g (87%) of (1R8,2R*,3R*,4S*,6S*)-3-(4-fluorobenzyl)amino-tricyclo[2.2.1.0$^{2,6}$]heptane-1,3-dicarboxylic acid (5).

A solution of 0.31 g (1 mmol) of the latter in 20 mL of methanol was subjected to hydrogenolysis by hydrogen in the presence of Pd/C catalyst at room temperature and atmospheric pressure for 36 hrs. After completion the catalyst was filtered off and washed several times with boiling water to yield after evaporation of solvents 0.19 g (97%) of the title compound. m.p. >260° C.; MS, (−) ESI, [M-H]$^−$ = 196; [α]$_{25}^D$ = −10.5° (measured in water).

Elemental analysis for C$_9$H$_{11}$NO$_4$ 1 H$_2$O. Calculated: C, 50.18; H, 6.04; N, 6.51. Found: C, 50.07; H, 5.45; N, 6.32.

The second enantiomer to elute from chiral HPLC column (intermediate (4')) was converted in an analogous manner into (+)-(1R*,2R*,3R*,4S*,6S*)-3-amino-tricyclo[2.2.1.0$^{2,6}$]heptane-1,3-dicarboxylic acid. m.p. >260° C.; MS, (−) ESI, [M-H]$^−$=196; [α]$_{25}^D$=+9.6° (measured in water).

Elemental analysis for C$_9$H$_{11}$NO$_4$ 0.75 H$_2$O Calculated: C, 51.30; H, 5.93; N, 6.65 Found: C, 51.22; H, 5.36; N, 6.61

EXAMPLE 2

The synthesis of (+/−)-(1R*,2R*,3R*,4S*,6S*)-3-aminotricyclo[2.2.1.0$^{2,6}$]-heptane-1,3-dicarboxylic acid has been accomplished in accordance with Scheme 2. Starting material—racemic 3-oxo-tricyclo[2.2.1.0$^{2,6}$]heptane-1-carboxylic acid (1) was prepared according Chem.Ber., GE, 93, 1960, 2271–2281. The crude material of ~80% purity was used without further purification.

Intermediate (2)-2',5'-Dioxo-spiro{tricyclo[2.2.1.0$^{2,6}$]heptane-3,4'-imidazoline}-1-carboxylic Acid.

A mixture of 1.52 g (10 mmol) of ketoacid (1), 0.78 g (12 mmol) of KCN and 3.36 g (35 mmol) of (NH$_4$)$_2$CO$_3$ in 75 mL of water-ethanol (1:1) was stirred at 75° C. for 36 hrs (additional 2–4 mmol of KCN and 6–12 mmol of ammonium carbonate added after 18 hrs). After completion most of ethanol was evaporated, reaction mixture acidified to pH=1 with concentrated HCl. Upon cooling the mixture to 0° C., a white precipitate formed and was washed with ice-cold water and ethyl acetate and dried in vacuum affording ~1.32 g (6 mmol) of hydantoin. Additional 0.22 g (~1 mmol) was isolated after concentration of mother liquor to the total yield of 1.54 g (7 mmol) (88% on pure ketoacid 1). The product was used as such without additional purification.

Intermediate (7)—1'-(4-fluorobenzyl)-2',5'-dioxo-spiro{tricyclo[2.2.1.0$^{2,6}$]heptane-3,4'-imidazoline}-1-carboxylic Acid 4-fluorobenzyl Ester.

1.1 g (5 mmol) Of intermediate (2) was treated with an excess of p-fluoro-benzyl bromide (2.37 g, 12.5 mmol) in K$_2$CO$_3$ (1.73 g, 12.5 mmol)—DMF (30 mL) system at 25° C. for 36 hrs. After completion the mixture was diluted to 500 mL with water and extracted with 2×250 mL of ethyl acetate. The extracts were washed with water, dried over sodium sulfate and concentrated in vacuum to give 1.47 g (67%) of title product (7).

4.5 g of intermediate (7) was chromatographed using HPLC (Primesphere 10 Silica column 50×250 mm, 95 mL/min, 35% ethyl acetate/hexane) to produce two racemic mixtures in a ratio ~1.5–2:1 in a favor of precursor (8+8'). First fraction to elute, the one containing intermediate (8) was evaporated to afford 3.0 g of colorless foam.

(+/−)-(1R*,2R*,3R*,4S*,6S*)-3-aminotricyclo[2.2.1.0$^{2,6}$]heptane-1,3-dicarboxylic Acid 0.88 g Of a racemic intermediate (8+8') (2 mmol) was subjected to a hydrolysis in a stirred mixture of 2.5 N NaOH (30 mL)—methanol (10 mL) in a stainless steel autoclave at 160° C. for 32 hrs. After completion of the reaction methanol was evaporated, the mixture was extracted with ethyl acetate. The water layer was acidified to pH=3–3.4 and evaporated to dryness. Dry solid was reconstituted with minimal amount of cold acidic (pH=3) water to dissolve inorganics and filtered to afford after washing with ethyl acetate and drying 0.33 g (85%) of the title. m.p. >260° C.; MS, (−) APCI, [M-H]$^−$=196.

Elemental analysis for C$_9$H$_{11}$NO$_4$ 1.25 H$_2$O. Calculated: C, 49.16; H, 6.15; N, 6.37. Found: C, 49.09; H, 5.86; N, 6.23.

What is claimed:

1. A process for preparation of a bridged tricyclic compound of the formulae:

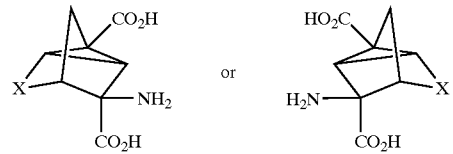

wherein
X is (CH$_2$)$_n$, O, S, SO, SO$_2$ or CR$^1$R$^2$;
n is 1 or 2;
R$^1$ and R$^2$ are, independently, hydrogen, halogen, hydroxy, alkyl of one to six carbon atoms, alkoxy of one to six carbon atoms, or R$^1$ and R$^2$, taken together with the carbon to which they are attached, form cycloalkyl of three to six carbon atoms, an alkylidene of up to six carbon atoms or a carbonyl;
the process comprising the steps of:
a) treating keto-acid of formula (1):

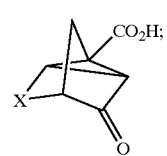

(1)

in the presence of ammonium carbonate and an alkali metal cyanide in a volume of organic solvent/water to give a spiro-fused hydantoin as a mixture of diastereomers having the formula (2);

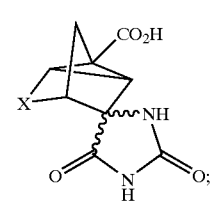

(2)

b) treating the spiro-fused hydantoin mixture of diastereomers (2) with an appropriate benzylic halogenide or sulfonate and alkali metal carbonate in an aprotic solvent to provide tri-substituted diastereomeric mixture of hydantoins (3);

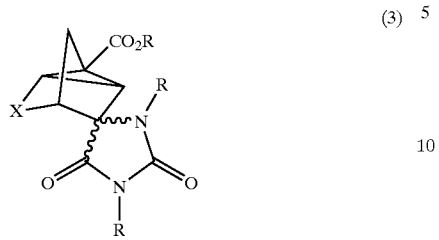
(3)

wherein R represents the benzyl residue of the corresponding benzylic halogenide or sulfonate;

c) separating the exo- and endo-racemic pairs of tri-substituted diastereomeric mixture of hydantoins (3) to yield the racemic mixture of (4) and (4');

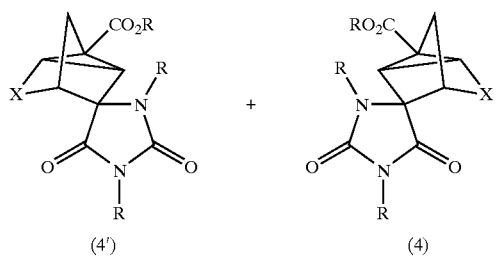
(4')            (4)

d) resolving the racemic mixture of (4) and (4') on a chiral column to produce both enantiomers (4) and (4') in an enantiomerically pure form;

e) treating intermediates (4), (4'), or a mixture thereof, with base to provide enantiomers of the formulae (5) and (5'):

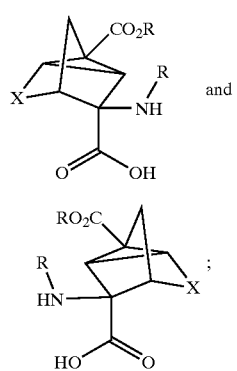
(5')

(5)

f) treating the compounds (5) and (5') with a palladium on carbon catalyst to provide the dextro-(+) and levorotatory (−) forms of the compounds (6') and (6).

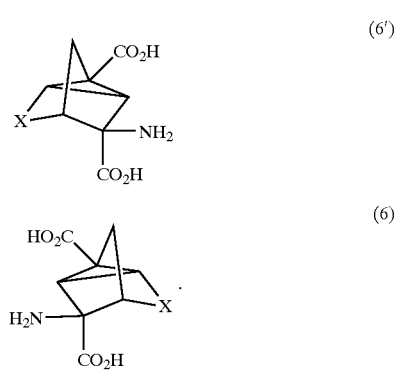
(6')

(6)

2. The process according to claim 1 wherein the volume of an organic solvent/water is present at a ratio of from about 1:1 to about 4:1.

3. The process according to claim 1 wherein the volume of an organic solvent/water is present at a ratio of from about 2.5:1 to about 1.5:1.

4. The process according to claim 1 wherein the organic solvent is selected from the group of acetonitrile, acetone, tetrahydrofuran, dimethylformamide, N-methylpyridine, N-methylpyrrolidone, dimethylsulfoxide, sulfalane, $C_1$–$C_8$ alkanols, glymes, or $C_2$–$C_8$ glycols.

5. The process according to claim 1 in which the bridged tricyclic compound is (+/−)-3-exo-aminotricyclo[2.2.1.0$^{2,6}$] heptane-1,3-endo-dicarboxylic acid or a pharmaceutically acceptable salt thereof.

6. The process according to claim 1 in which the bridged tricyclic compound is (−)-3-exo-aminotricyclo[2.2.1.0$^{2,6}$] heptane-1,3-endo-dicarboxylic acid or a pharmaceutically acceptable salt thereof.

7. The process according to claim 1 in which the bridged tricyclic compound is (+)-3-exo-aminotricyclo[2.2.1.0$^{2,6}$] heptane-1,3-endo-dicarboxylic acid or a pharmaceutically acceptable salt thereof.

8. The process according to claim 1 wherein step e) is conducted at a temperature of from about 60° C. to about 180° C.

9. The process according to claim 1 wherein the base used in step e) is selected from the group of barium hydroxide, calcium hydroxide, lithium hydroxide, sodium hydroxide, or potassium hydroxide.

* * * * *

UNITED STATES PATENT AND TRADEMARK OFFICE
CERTIFICATE OF CORRECTION

PATENT NO. : 6,689,904 B2
DATED : February 10, 2004
INVENTOR(S) : Alexander Alexei Greenfield and John Anthony Butera It is certified that error appears in the above-identified patent and that said Letters Patent is hereby corrected as shown below:

<u>Title page,</u>
Item [60], Related U.S. Application Data, "60/302,251" should read -- 60/302,346 --.

Signed and Sealed this

Twenty-ninth Day of June, 2004

JON W. DUDAS
*Acting Director of the United States Patent and Trademark Office*